(12) United States Patent
Koehler et al.

(10) Patent No.: US 8,131,040 B2
(45) Date of Patent: Mar. 6, 2012

(54) ARTIFACT CORRECTION FOR MOTION ARTIFACTED IMAGES ASSOCIATED WITH THE PULMONARY CYCLE

(75) Inventors: Thomas Koehler, Nordeerstedt (DE); Peter Koken, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 510 days.

(21) Appl. No.: 12/377,915

(22) PCT Filed: Jul. 24, 2007

(86) PCT No.: PCT/US2007/074203
§ 371 (c)(1),
(2), (4) Date: Feb. 18, 2009

(87) PCT Pub. No.: WO2008/024584
PCT Pub. Date: Feb. 28, 2008

(65) Prior Publication Data
US 2010/0239134 A1    Sep. 23, 2010

Related U.S. Application Data

(60) Provisional application No. 60/823,103, filed on Aug. 22, 2006.

(51) Int. Cl.
*G06K 9/00* (2006.01)
(52) U.S. Cl. ......... 382/128; 382/131; 600/407; 600/410
(58) Field of Classification Search .................. 382/128, 382/131, 132; 600/407, 410
See application file for complete search history.

(56) References Cited

U.S. PATENT DOCUMENTS

| 6,490,476 B1 | 12/2002 | Townsend et al. |
| 2002/0122528 A1* | 9/2002 | Besson ............................ 378/4 |
| 2005/0113702 A1 | 5/2005 | Salla et al. |
| 2005/0201509 A1* | 9/2005 | Mostafavi et al. ................ 378/8 |
| 2006/0178575 A1 | 8/2006 | Piacsek et al. |
| 2006/0198490 A1 | 9/2006 | Tsuyuki et al. |

FOREIGN PATENT DOCUMENTS

| EP | 1420269 A1 | 5/2004 |
| EP | 1834585 A2 | 9/2007 |
| WO | 2007015199 A2 | 2/2007 |

OTHER PUBLICATIONS

Clinical Trials.gov; Effect of Respiratory Motion on Positron Emission Tomography Imaging; Completed Study Sponsored by National Institutes of Health Clinical Center. http://www.clinicaltrials.gov/ct/gui/show/NCT00088361.

Pan, T., et al.; Attenuation Correction of PET Images with Respiration-Averaged CT Images in PET/CT; 2005; J. Nuclear Medicine; 46:1481-1487.

\* cited by examiner

*Primary Examiner* — Francis M Legasse, Jr.

(57) ABSTRACT

A diagnostic imaging system (8) images a subject at a preselected phase point (46) which occurs in one or more successive pulmonary cycles. A breathing monitor (44) monitors a cyclic physiological parameter in the pulmonary cycle and generates a cyclic pulmonary phase indicative signal. A CT scanner (12) is disposed adjacent an examination region (28) to generate transmission radiation data. A data processor (60) reconstructs an attenuation map (96) from the transmission data by weighting the transmission radiation data such that each of the pulmonary phases contributes substantially equally to the attenuation map.

20 Claims, 7 Drawing Sheets

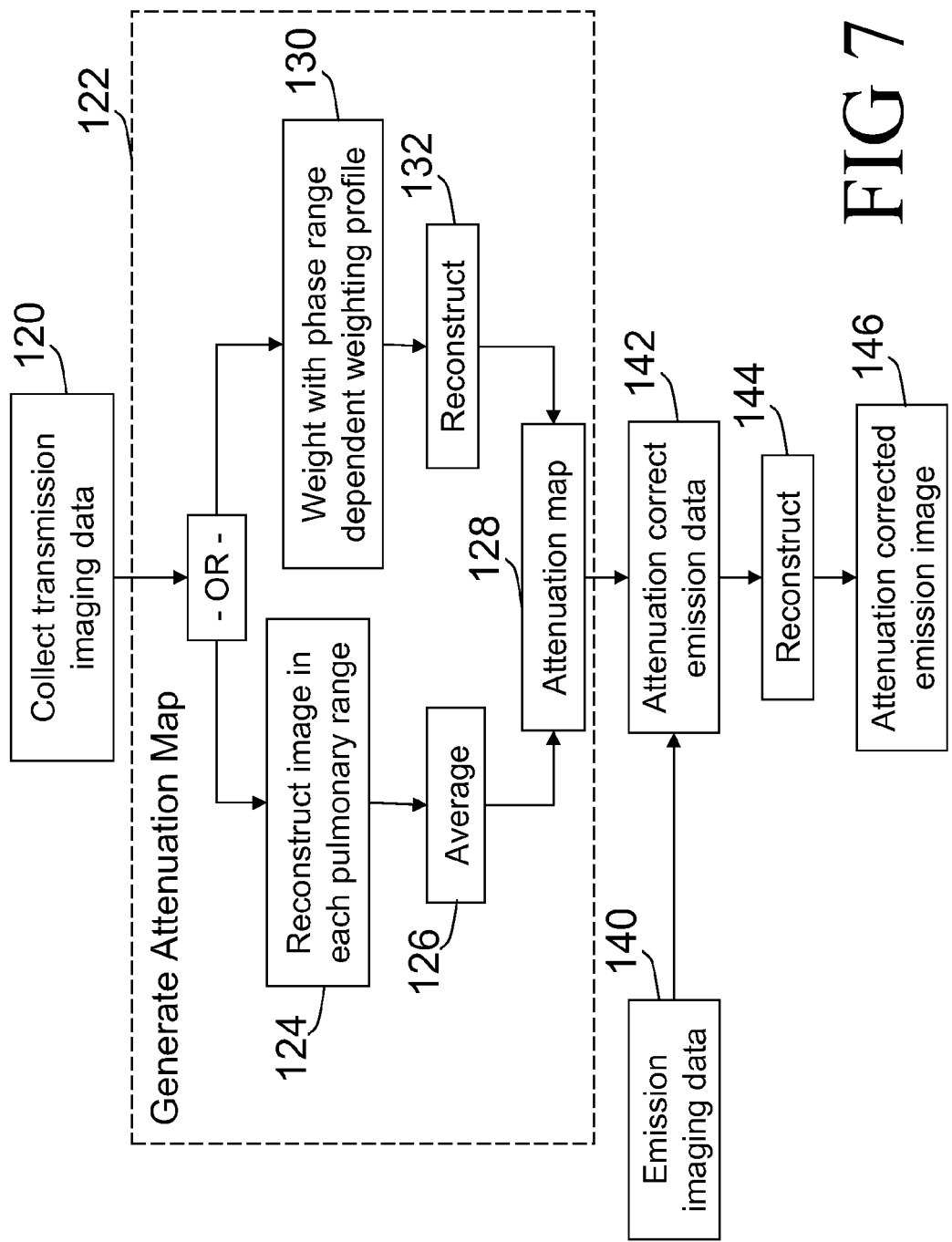

ARTIFACT CORRECTION FOR MOTION ARTIFACTED IMAGES ASSOCIATED WITH THE PULMONARY CYCLE

CROSS REFERENCE TO RELATED APPLICATIONS

This application claims the benefit of U.S. provisional application Ser. No. 60/823,103 filed Aug. 22, 2006, which is incorporated herein by reference.

The present application relates to the diagnostic imaging arts. It finds particular application in conjunction with the Single Photon Emission Tomography (SPECT) systems with attenuation compensation and will be described with particular reference thereto. It will be appreciated that the invention is also applicable to other imaging systems such as Positron Emission Tomography (PET) systems, and the like. We will refer to such systems as emission tomography systems.

Emission radiation imaging employs a source of radioactivity to image a patient. Typically, a radiopharmaceutical is injected into the patient. Radiopharmaceutical compounds contain a radioisotope that undergoes gamma-ray decay at a predictable rate and characteristic energy. One or more radiation detectors are placed adjacent to the patient to monitor and record emitted radiation. Sometimes, the detector is rotated or indexed around the patient to monitor the emitted radiation from a plurality of directions. Based on information such as detected position and energy, the radiopharmaceutical distribution in the body is determined and an image of the distribution is reconstructed to study the circulatory system, radiopharmaceutical uptake in selected organs or tissue, and the like.

In medical studies, generally, as the emission data normally contains inaccuracies caused by varying absorption characteristics of the patient's anatomy, an attenuation map (transmission map) either generated by a transmission radiation source or a CT image is used to provide additional attenuation information to correct the emission data.

Typically, the emission tomography scan is performed without preliminary gating, which implies that the collected data correspond to the average motion state over the breathing cycle. Thus, in one approach, to obtain attenuation maps, the patients are asked to hold their breaths during the CT scan, for example, at midexpiration or take a shallow breath. Because the free breathing state in the emission tomography imaging differs from the breath hold state in the CT imaging, the CT images do not accurately align with the emission data. This might result in inaccurate diagnostics and quantization of tumors in the emission images.

In another approach, to parallel the data acquisition protocol of the emission tomography scan, during the CT scan, the patient continues breathing. A low pitch is used to ensure that every voxel is illuminated by the cone-beam over at least one complete breathing cycle. However, the CT scan is far faster than the nuclear imaging scan. Typically, only one or two breathing cycles are captured for each object point. The standard reconstruction provides only a poor average over the motion state which causes artifacts, which look like mushrooms in saggital or coronal cross-sections.

The present application provides new and improved methods and apparatuses which overcome the above-referenced problems and others.

In accordance with one aspect, an imaging system for imaging at a preselected pulmonary range which occurs in one or more successive pulmonary cycles is disclosed. A breathing monitor monitors a cyclic physiological parameter in the pulmonary cycle and generates a cyclic pulmonary phase indicative signal. A source of transmission radiation data is provided. A data processor reconstructs an attenuation map from the transmission data by weighting the transmission radiation data such that each of the pulmonary phases contributes substantially equally to the attenuation map.

In accordance with another aspect, an imaging method for imaging at a preselected pulmonary range which occurs in one or more successive pulmonary cycles is disclosed. A cyclic physiological parameter in the pulmonary cycle is monitored. A cyclic pulmonary phase indicative signal is generated. Transmission radiation data is generated. An attenuation map is reconstructed from the transmission data by equally weighting the transmission data in each of the plurality of pulmonary phases.

In accordance with another aspect, a method of emission imaging is disclosed. Transmission imaging data is collected over cyclically repeating pulmonary ranges of a pulmonary cycle. An attenuation map is generated with a substantially equal contribution from each phase point. The emission data is corrected with the attenuation map. The attenuation corrected emission data is reconstructed into a diagnostic image.

One advantage is that artifacts are reduced in attenuation corrected emission radiation images.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
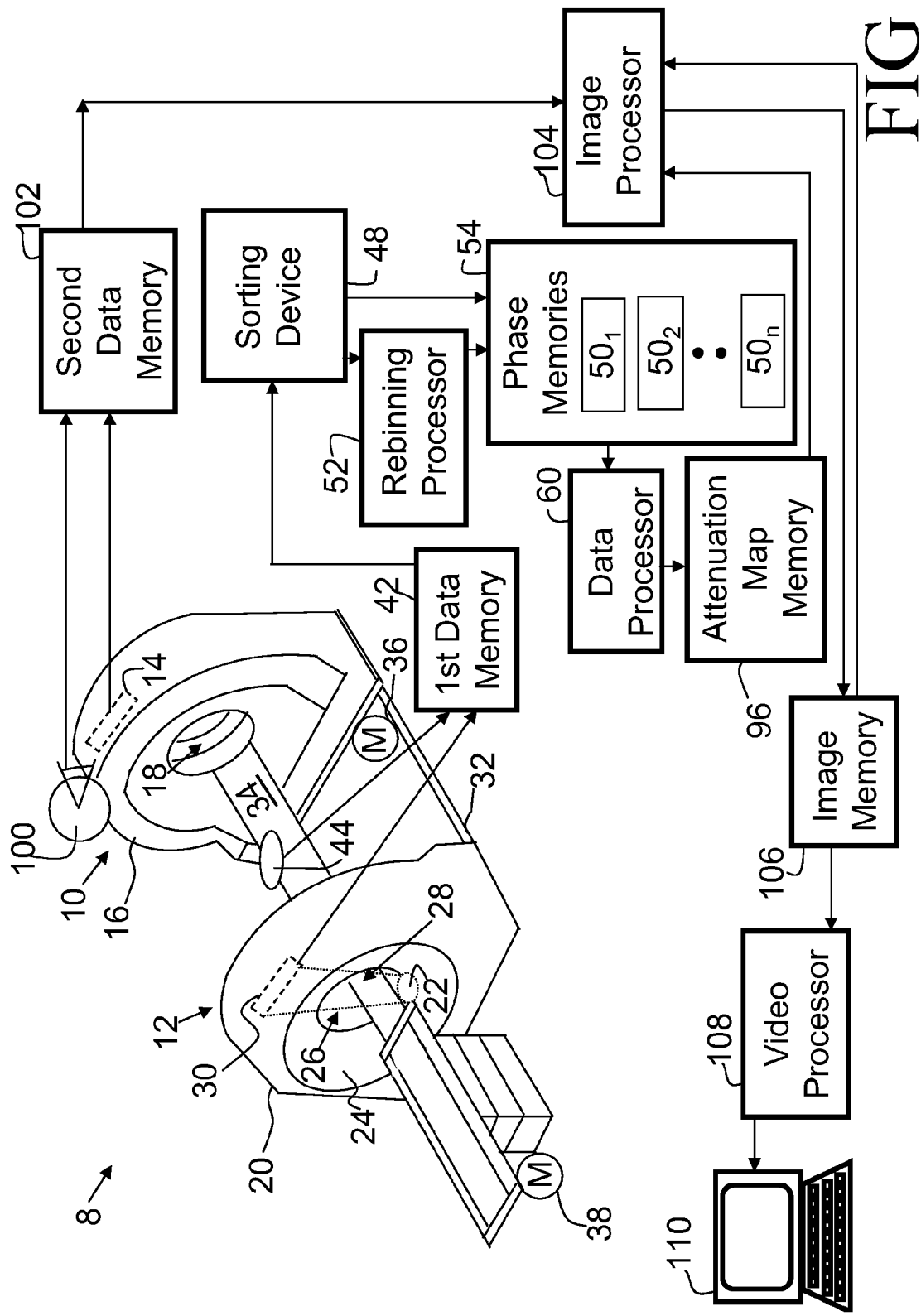
FIG. 1 is a diagrammatic illustration of an imaging system.

With reference to FIG. 1, an imaging system 8 includes an emission imaging system 10 such as a SPECT or PET scanner and a CT scanner 12. More specifically, one or more nuclear detection heads 14 are carried by a rotatable gantry 16 to detect radiation events emanating from a region of interest or examination region 18. Each detection head 14 includes two-dimensional arrays of detector elements, such as a scintillator and an array of light sensitive elements, e.g. photomultiplier tubes, photodiodes, and the like. Direct x-ray to electrical converters, such as CZT elements, are also contemplated. Alternatively, particularly in a PET scanner, the examination region is typically surrounded by a ring of stationary detector heads. Each head 14 includes circuitry for converting each radiation response into a digital signal indicative of its location (x, y) on the detector face, its energy (z), angular position of the head, and detection time. The location of an event on the detector is resolved and/or determined in a two dimensional (2D) Cartesian coordinate system with nominally termed x and y coordinates. However, other coordinate systems are contemplated. In the SPECT scanner, a collimator controls the direction and angular spread, from which each element of the detector can receive radiation, i.e., the detector can receive radiation only along known rays. Thus, the determined location on the detector at which radiation is detected and the angular position of the head 14 define the nominal ray along which each radiation event occurred.

As the emission data normally contains inaccuracies caused by varying absorption characteristics of the patient's anatomy, in one embodiment, the CT scanner 12 is utilized to provide additional attenuation information to correct the emission data. The CT scanner 12 includes a non-rotating gantry 20. A radiation source or sources 22, such as an x-ray tube, is mounted to a rotatable gantry 24. A bore 26 defines an examination region 28 of the CT scanner 12. A non-bore system, such as L-shape, arc, and other are also contemplated. An array of radiation detectors or a radiation detector 30 is disposed on the rotatable gantry 24 to receive radiation from the x-ray tube 22 after the x-rays transverse the examination region 28. Tracks 32 extend in parallel to a longitudinal axis of a subject support or couch 34, thus enabling the emission imaging scanner 10 and CT scanner 12 to form a closed system. A moving means 36, such as a motor and a drive, is provided to move the PET scanner 10 in and out of the closed position. A couch moving means 38, such as a motor and a drive, provides a longitudinal movement and vertical adjustment of the couch 34 in the examination regions 18, 28.

In one embodiment, the emission imaging system 10 and the CT scanner 12 employ a common gantry. In such system, the detection is performed simultaneously or interleaved. In another embodiment, the CT and emission imaging are performed in different imaging sessions.

With continuing reference to FIG. 1, as the rotatable gantry 24 of the CT scanner 12 rotates at a constant speed, a subject or patient, which is positioned on the couch 34, is moved into the examination region 28, where the CT image is taken. The drive 38 advances and/or retracts the subject support 34 to achieve the desired positioning of the subject within the examination region 28. Typically, during scanning, some portion of the radiation passing along each projection is absorbed by the imaging subject to produce a generally spatially varying attenuation of the radiation. The detector elements of the radiation detector array 30 sample the radiation intensities across the radiation beam to generate radiation absorption projection data. As the gantry 24 rotates so that the radiation source 22 revolves around the examination region 28, a plurality of angular views of projection data are acquired, collectively defining a projection data set that is stored in a first or CT data memory 42. The acquired data is referred to as projection data since each detector element detects a signal corresponding to an attenuation line integral taken along a line, ray, narrow cone, or other substantially linear projection extending from the source to the detector element. The radiation detector 30 is shown mounted on the rotatable gantry 24 in FIG. 1; however, it is also contemplated to replace the detector array 30 by a two-dimensional band of x-ray detector elements mounted around the stationary gantry 20. In one embodiment, the radiation detector 30 includes flat panel detectors.

In another embodiment, a helical projection data set is acquired by rotating the gantry 24 simultaneously with continuous linear motion of the couch 34 to produce a helical trajectory of the radiation source 22 around the imaging subject disposed on the couch 34.

For a source-focused acquisition geometry in a multi-slice scanner, readings of the attenuation line integrals or projections of the projection data set stored in the CT data memory 42 can be parameterized as $P(\alpha,\beta,n)$ where $\alpha$ is the source angle of the radiation source 22 determined by the position of the rotatable gantry 24, $\beta$ is the angle within the fan ($\beta \in [-\Phi/2, \Phi/2]$ where $\Phi$ is the fan angle), and n is the detector row number.

Figure 2:
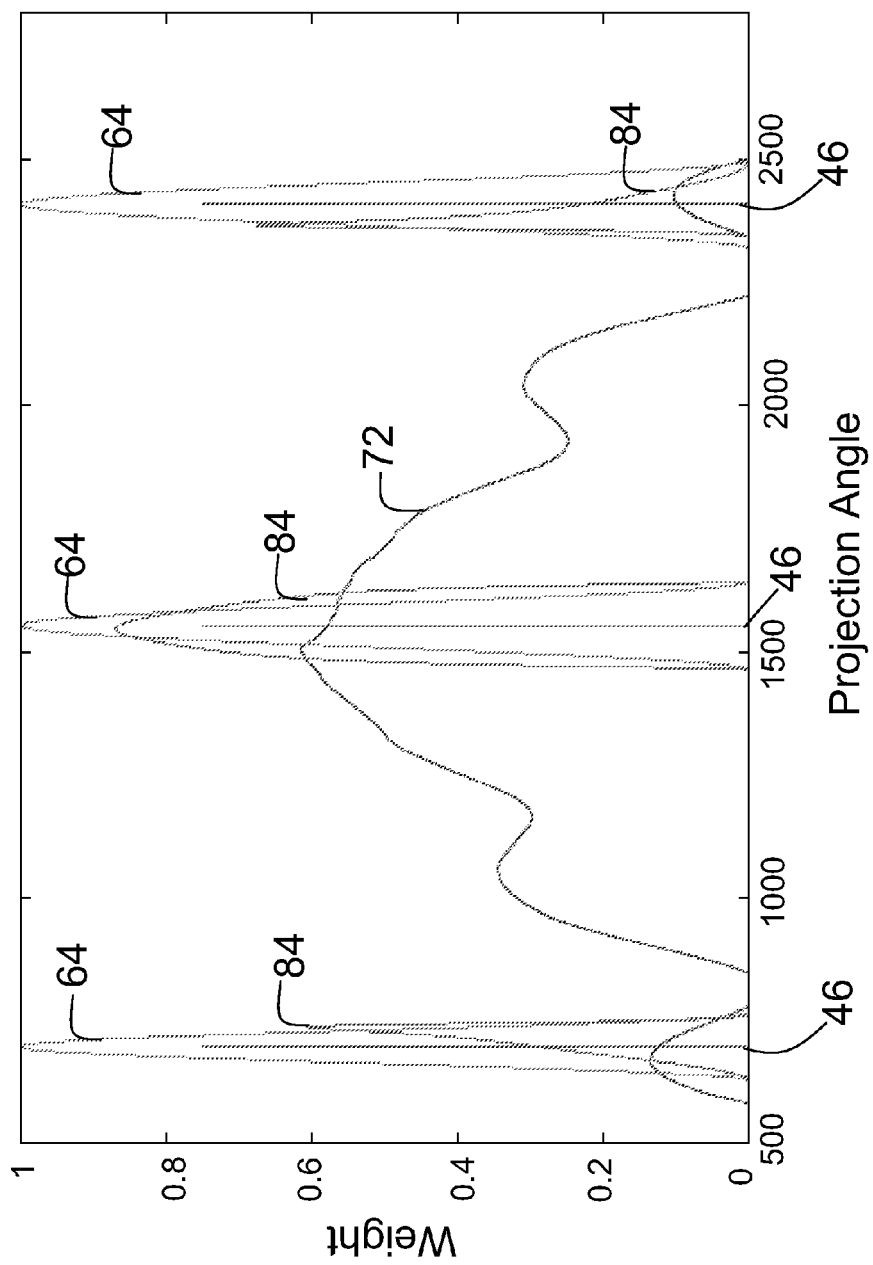
FIG. 2 is a diagrammatic illustration of a non-normalized weighting profile for a sampling window.

With continuing reference to FIG. 1 and further reference to FIG. 2, a cycle monitor 44 monitors prespecified biological cycles of the patient. In one embodiment, the cycle monitor 44 monitors patient's respiratory cycle and detects phase points 46. For example, a respiratory sensing belt is connected with a balanced bridge type pressure transducer which produces an electrical signal that varies in amplitude with the respiratory cycle. The position of the phase point 46 is selected by the clinician according to the motion characteristic of the lungs and the required diagnostic information.

In one embodiment, a respiratory marker, which is coupled with respiration of the imaging subject, moves with the respiration. The marker is arranged to intersect the images acquired at different times and at different positions along the scanner axis and is detectable as a marker feature in the images so the positions of the marker features in the images can be determined. In this manner, the respiratory monitoring data is embedded directly with the imaging data.

In another embodiment, the CT scanner itself is used to generate a gating signal from the images of the subject under examination. The same data is used to generate the gating signal and images. For example, the scanner generates a pulmonary gating signal based on maxima periodic motion of the subject or minima periodic motion of the subject.

A sorting device, processor, mechanism or other means 48 sorts the attenuation data into data sets $50_1, 50_2, \ldots, 50_n$ collected during each of the selected breathing phases, i.e. breathing phase specific data sets. In one embodiment, a re-binning processor 52 re-bins the breathing phase specific data from cone to parallel beam geometry into a set of parallel views. The parallel views are projected into the axial plane i.e., perpendicular to the rotation axis. Particularly for breathing phases defined by a short temporal window, the data for one breathing phase corresponds to data collected over short arc segments in one or more rotations and breathing cycles. The arc segments of data individually are too small to be a full data set. To generate a full data set, data is collected over several breathing cycles and, if necessary, interpolated. The breathing phase specific data sets are stored in corresponding phase memories 54.

Figure 3:
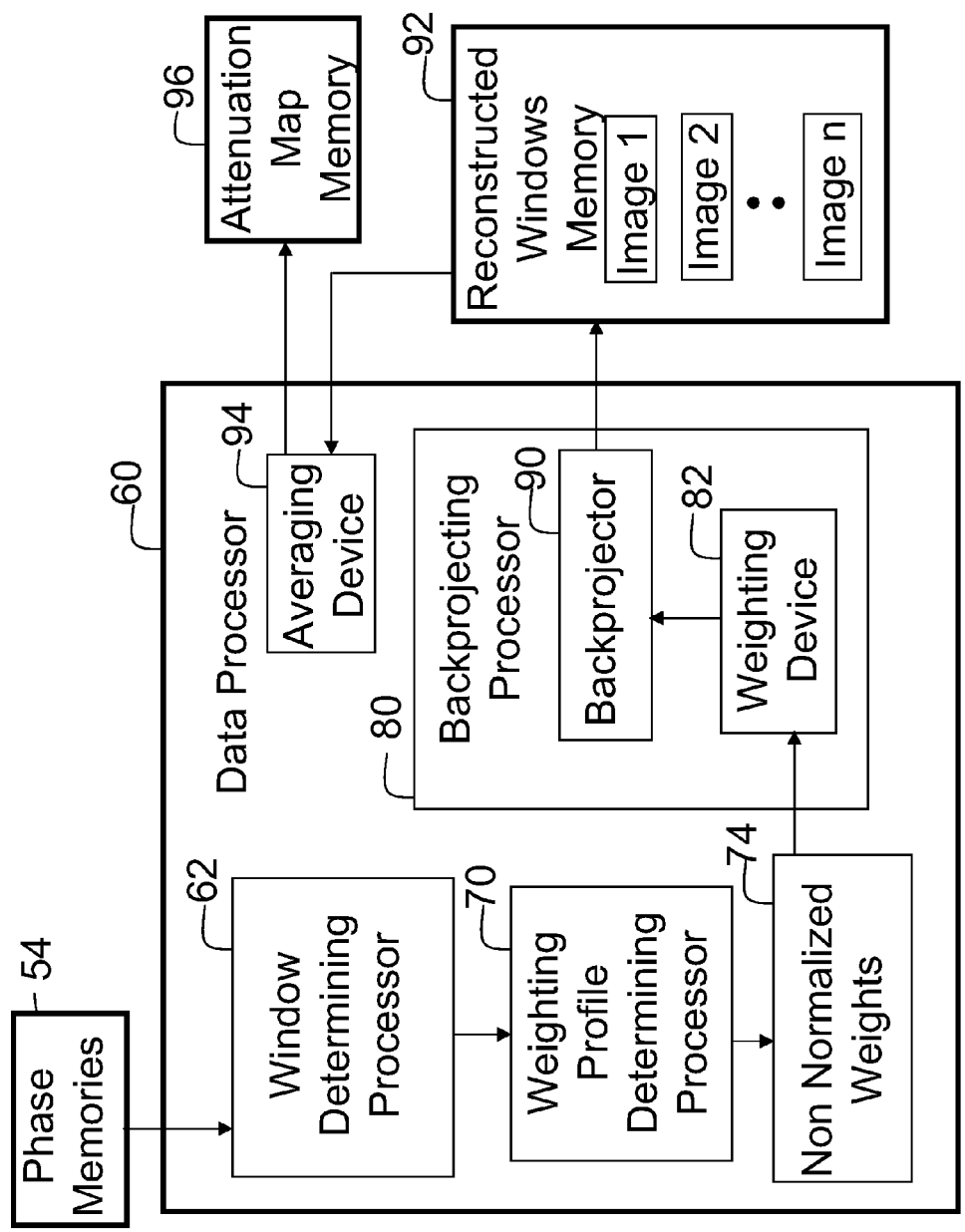
FIG. 3 is a diagrammatic illustration of a detailed portion of an imaging system.

With continuing reference to FIGS. 1 and 2 and further reference to FIG. 3, a data processor 60 reconstructs a 3D transmission radiation image or attenuation maps for each individual selected breathing phase. More specifically, a sampling window determining processor, device, mechanism, algorithm or other means 62 determines or selects a sampling window 64 surrounding a corresponding phase point 46. In one embodiment, each phase point 46, represented by a vertical line, lies substantially central in the associated window. A weighting profile determining processor, device, mechanism, algorithm or other means 70 determines a non-normalized weighing profile 72 for all voxels lying in the window. Non-normalized weights are stored in a non-normalized weights memory 74.

A backprojecting processor, device, mechanism, algorithm or other means 80 performs a normalized weighted backprojection on received projections into a 3D image representation or attenuation map. In one embodiment, a weighting processor, device, mechanism, algorithm or other means 82 combines non-normalized weights determined for each sampling window 64 with other weights typically used in the reconstruction process to generate normalized weights or normalized weighting profile 84 and applies the normalized weights to each voxel of a corresponding window.

For example, when two or more π-partners intersect the voxel v at the same angle θ, the redundant rays can be interpolated to increase resolution. The redundant rays may traverse the voxel from opposing directions or be slightly offset from each other. The weighting processor 82 normalizes multiples of π-partners on the fly. Example of other weights given during reconstruction includes aperture weights. The aperture weights given to each voxel for a reading are calculated by one of known techniques and are typically dependent on the relative position of the voxel with respect to the acquisition system. A backprojector 90 backprojects the normalized projections into 3D images which are stored into corresponding reconstructed images memories 92. An averaging processor, device, mechanism, algorithm or other means 94 averages the stored reconstructed images to receive the image representing the breathing average. Each voxel value stored in an attenuation map memory 96 is indicative of attenuation of radiation by tissue in a corresponding volume to be used in phases of a breathing cycle. By averaging the images from each of the preliminary phases equally, each pulmonary phase contributes equally to the attenuation map 96.

Figure 4:
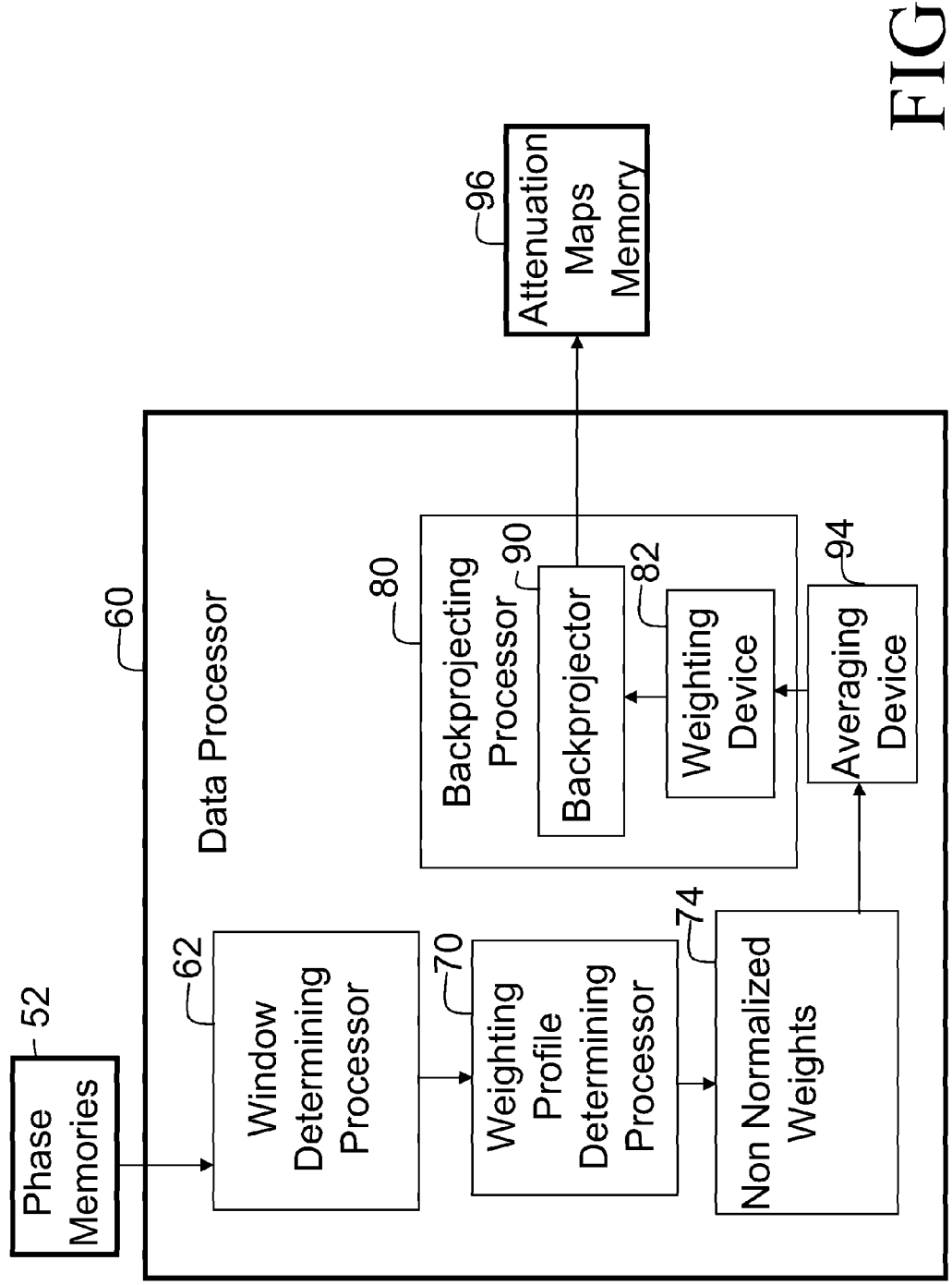
FIG. 4 is a diagrammatic illustration of another detailed portion of an imaging system.
Figure 5:
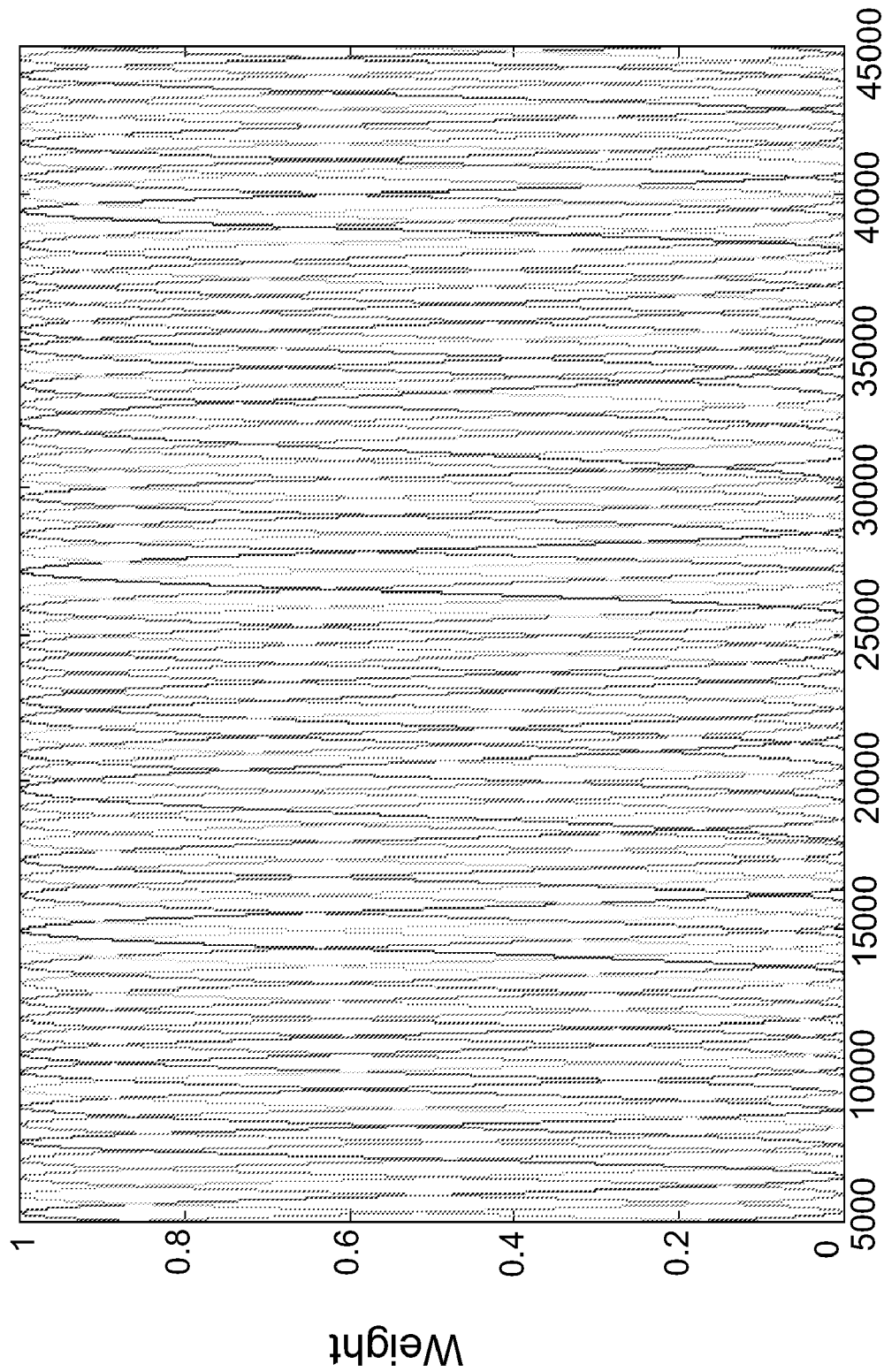
FIG. 5 shows non-normalized weighting profiles for a plurality (about 20) of sampling windows.
Figure 6:
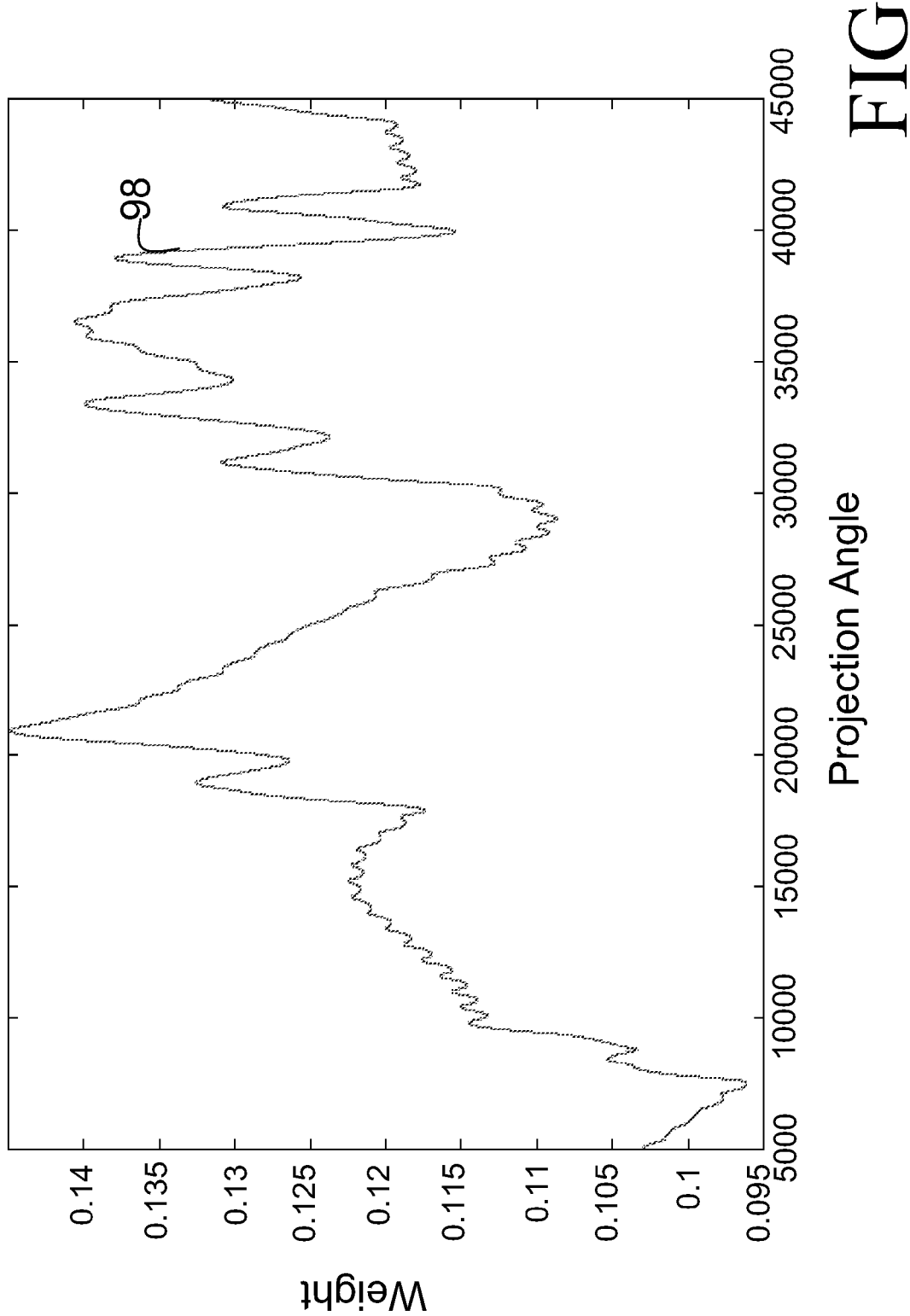
FIG. 6 shows a graph representing an average of non-normalized weighting profiles of FIG. 5; and, FIG. 7 illustrates steps of a method of emission radiation imaging.

With reference to FIGS. 4-6, the weighting profile determining processor 70 determines non-normalized weighting profiles for selected sampling windows. When data is collected for a large number of pulmonary phases, in a multiplicity of sequential sampling windows, a multiplicity of normalized weighting profiles are applied sequentially. FIG. 5 shows the large number of sequential weighting profiles. If, for example, there are 20 pulmonary phases, 20 weighting profiles are repeated cyclically. The averaging device 94 averages the non-normalized weights for the selected windows to generate an average weighting profile 98 illustrated in FIG. 6. The weighting device 82 combines the non-normalized weights determined for the selected windows with other weights typically used in the reconstruction process and described above to receive normalized weights. The backprojector 90 backprojects the normalized averaged projections into the attenuation map memory 96. By reducing the contribution of each backprojected view in inverse proportion to the number of views generated in its pulmonary phase, each pulmonary phase contributes equally to the attenuation map 96.

Other data processing techniques which generate an attenuation map which is equally weighted over pulmonary phases are also contemplated.

With continuing reference to FIG. 1, the subject support table 34 with the subject is moved into the emission examination region 18 to position the subject to take the emission image. Typically, prior to the examination, the subject to be imaged is injected with one or more radiopharmaceuticals or radioisotopes. Few examples of such isotopes are Tc-99m, Ga-67, and In-111. The presence of the radiopharmaceuticals within the object produces emission radiation from the object. During the data collection, the emission radiation detector heads 14 are typically rotated in steps or continuously around the examination region 18 to collect the projection emission data at a multiplicity of projection directions. In one embodiment, the heads are rotated over an arc of 360° divided by the number of heads. The projection emission data, e.g. the location (x, y) on the detector head, energy (z), and an angular position (θ) of each detection head 14 around the examination region 18 (e.g., obtained from an angular position resolver 100) are stored in a second or emission data memory 102.

An image processor, algorithm, mechanism or other means 104 iteratively reconstructs a 3D image representation in an image memory 106. For each ray, along which emission data is received, the image processor 104 calculates a corresponding ray through a corresponding attenuation map array stored in the phase attenuation map memories 96. Each ray of the emission data is weighted or corrected in accordance with the attenuation factors.

A video processor 108 retrieves slices, projections, 3D renderings, and other information from the image memory and appropriately formats an image representation for display on a monitor or monitors 110. Of course, a printer or other output device may also be used to present data in a convenient format.

In one embodiment, the user selects the phases via, for example, a graphical user interface integrated with the monitor 110 or any other appropriate personal computer, PDA and the like.

With reference to FIG. 7, looking now to a method of generating attenuation corrected emission images, transmission image data is collected 120, such as by the CT scanner 12. An attenuation map is generated 122 from the transmission image data. In a first method of generating the attenuation map, the transmission image data collected in each of a plurality of pulmonary ranges over a plurality of pulmonary cycles is reconstructed 124. These images are then averaged 126 to generate an attenuation map 128 in which transmission image data from each of the pulmonary ranges contributes equally. Alternately, each view of the transmission image data is weighted 130 with a phase range dependent weighting profile such as profile 98. These views are reconstructed 132 such as by using filtered or convolution weighting and backprojection. Of course, the phase range dependent weighting profile and the filter or convolution functions may be combined and a single weighting step performed.

Emission data is collected 140. The emission data is corrected 142 with the attenuation map 128. The attenuation correction emission data is then reconstructed 144 to generate an attenuation corrected emission image 146.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging system for imaging at a preselected range of a pulmonary cycle which occurs in one or more successive pulmonary cycles, the imaging system comprising:
   a breathing monitor which monitors a cyclic physiological parameter in the pulmonary cycle and generates a cyclic pulmonary phase indicative signal;
   a source of transmission radiation data; and
   a data processor which reconstructs an attenuation map from the transmission data by weighting the transmission radiation data such that each of the pulmonary phases contributes substantially equally to the attenuation map.

2. The system as set forth in claim 1, further including:
   a window selecting device which selects a sampling window corresponding to each preselected phase point.

3. The system as set forth in claim 1, further including:
   a sorting device which sorts the transmission radiation data into radiation data sets corresponding to each of a plurality of the cyclic pulmonary phases;
   a backprojecting device which backprojects the transmission data from each of the pulmonary phases into a corresponding pulmonary phase image in a reconstructed images memory; and an averaging device which averages the reconstructed pulmonary phase images with equal weighting into the attenuation map.

4. The system as set forth in claim 1, wherein the data processor programmed to:
weight the transmission radiation data in each pulmonary phase in inverse proportion to an amount of the transmission data collected in each of the pulmonary phases relative to other pulmonary phases;
reconstruct the weighted transmission radiation data into the attenuation map.

5. The system as set forth in claim 1, further including:
a backprojecting device which, based at least on the averaged non-normalized weighting profile, determines normalized weights for the plurality of the sampling windows and backprojects the transmission radiation data using the normalized weights into the attenuation map.

6. The system as set forth in claim 1, wherein the data processor includes:
a backprojector which backprojects the transmission radiation data into the attenuation map memory; and
a weighting device which weights the transmission radiation data in inverse proportion to an amount of transmission radiation data generated at the same pulmonary phase by viewing angle such that the transmission radiation data from each of the pulmonary cycle phases contribute substantially equally to the attenuation map.

7. The system as set forth in claim 1, further including:
an emission imaging scanner to generate emission radiation data; and
an image processor which corrects the emission radiation data with the attenuation map and reconstructs the attenuation corrected emission radiation data into an image representation.

8. The system as set forth in claim 2, further including:
a weighting profile determining processor which determines non-normalized weighting profiles for a plurality of the samples windows.

9. The system as set forth in claim 8, further including:
an averaging device which averages the determined non-normalized weighting profiles for the plurality of the sampling windows; and
a backprojecting device which, based at least on the averaged non-normalized weighting profile, determines normalized weights for the plurality of the sampling windows and backprojects the transmission radiation data using the normalized weights into the attenuation map.

10. An imaging method for imaging at a preselected range of a pulmonary cycle which occurs in one or more successive pulmonary cycles, the method comprising:
monitoring a cyclic physiological parameter in the pulmonary cycle;
generating a cyclic pulmonary phase indicative signal;
generating transmission radiation data; and
reconstructing an attenuation map from the transmission data by equally weighting the transmission data in each of the plurality of pulmonary phases.

11. The method as set forth in claim 10, further including:
selecting a sampling window corresponding to each of a plurality of preselected phase points in the pulmonary cycle.

12. The method as set forth in claim 10, further including:
sorting the transmission radiation data into radiation data sets corresponding to each of a plurality of the pulmonary phase points;
backprojecting the transmission data for each pulmonary phase point into a corresponding reconstructed image;
combining the reconstructed images with substantially equal weighting into the attenuation map.

13. The method as set forth in claim 10, wherein unequal amounts of transmission radiation data are collected in each pulmonary phase.

14. The method as set forth in claim 10, wherein reconstructing the attenuation map includes:
weighting the transmission data in accordance with at least a relative amount of transmission data collected in its pulmonary phase relative of other pulmonary phases; and
backprojecting the weighted transmission data to generate the attenuation map with a substantially equal contribution from each pulmonary phase.

15. The method as set forth in claim 11, further including:
determining non-normalized weighting profiles for each of the sampling windows.

16. The method as set forth in claim 15, further including:
averaging the determined non-normalized weighting profiles for the plurality of the sampling windows.

17. The method as set forth in claim 16, further including:
based at least on the averaged non-normalized weighting profile, determining normalized weightings for the plurality of the sampling windows;
normalizing the transmission radiation data with the determined normalized weighting; and
backprojecting the normalized transmission radiation data into the attenuation map.

18. An apparatus for emission imaging comprising:
one or more processors programmed to:
receive transmission imaging data over cyclically repeating phase ranges of a pulmonary cycle;
generate an attenuation map with a substantially equal contribution from the transmission imaging data collected during each of a plurality of different phase ranges;
collect emission data;
correct the emission data with the attenuation map; and
reconstruct the attenuation corrected emission data into a diagnostic image.

19. The apparatus as set forth in claim 18 wherein the processor is further programmed to:
(a) average with equal weighting images reconstructed from the collected transmission imaging data in each of the phase ranges to generate the attenuation map, and
(b) weight the collected transmission imaging data with a phase range dependent weighting function and backproject the weighted collected transmission data to generate the attenuation map.

20. A non-transitory computer readable medium carrying software which controls one or more processors to:
generate an attenuation map with a substantially equal contribution from transmission imaging data in each of a plurality of cyclically repeating ranges or motion states over a plurality of pulmonary cycles;
correct emission imaging data with the attenuation map; and
reconstruct the attenuation corrected emission imaging data into an image.

* * * * *